United States Patent
Ziegler et al.

(10) Patent No.: US 7,689,279 B2
(45) Date of Patent: Mar. 30, 2010

(54) PACING DEVICE FOR MINIMIZING VENTRICULAR PAUSES AFTER DELIVERY OF ATRIAL ANTI-TACHYCARDIA PACING THERAPY

(75) Inventors: Paul D. Ziegler, Minneapolis, MN (US); Douglas A. Hettrick, Blaine, MN (US); Paul G. Krause, St. Louis Park, MN (US); Katherine H. Anderson, Golden Valley, MN (US)

(73) Assignee: Medtronic, Inc., Minneapolis, MN (US)

( * ) Notice: Subject to any disclaimer, the term of this patent is extended or adjusted under 35 U.S.C. 154(b) by 497 days.

(21) Appl. No.: 11/271,387

(22) Filed: Nov. 10, 2005

(65) Prior Publication Data
US 2007/0106334 A1 May 10, 2007

(51) Int. Cl.
*A61N 1/00* (2006.01)
(52) U.S. Cl. .......................................................... 607/9
(58) Field of Classification Search .................. 607/5, 607/9, 14, 28, 122
See application file for complete search history.

(56) References Cited

U.S. PATENT DOCUMENTS

| | | | |
|---|---|---|---|
| 4,467,810 A | 8/1984 | Vollmann | |
| 5,181,511 A * | 1/1993 | Nickolls et al. | 607/14 |
| 5,456,706 A * | 10/1995 | Pless et al. | 607/122 |
| 5,620,466 A * | 4/1997 | Haefner et al. | 607/5 |
| 5,653,737 A | 8/1997 | van Lake | |
| 5,928,271 A | 7/1999 | Hess et al. | |
| 6,195,584 B1 * | 2/2001 | Hill et al. | 607/28 |
| 6,434,424 B1 | 8/2002 | Igel et al. | |
| 2002/0082657 A1 | 6/2002 | Stahmann et al. | |
| 2004/0138715 A1 | 7/2004 | van Groeningen et al. | |
| 2004/0220624 A1 | 11/2004 | Ritscher et al. | |

FOREIGN PATENT DOCUMENTS

EP 0753326 A 1/1997

OTHER PUBLICATIONS

International Search Report, PCT/US2006/060513, Nov. 25, 2008, 9 Pages.

* cited by examiner

*Primary Examiner*—George Manuel
(74) *Attorney, Agent, or Firm*—Stephen W. Bauer; Michael C. Soldner (57) ABSTRACT

A pacing control is used in a multiple-chamber cardiac pacing system, which, upon detecting an atrial arrhythmia, automatically switches to a special therapy mode and administers a selected anti-tachycardia pacing (ATP) therapy in the atrium, and which switches to a standard pacing mode following delivery of the ATP therapy. The pacing control adjusts the timing of pacing pulses to be delivered to the atrium and/or the ventricle to minimize any potential ventricular pauses that may result from the switch from the therapy mode to the standard pacing mode.

15 Claims, 5 Drawing Sheets

PACING DEVICE FOR MINIMIZING VENTRICULAR PAUSES AFTER DELIVERY OF ATRIAL ANTI-TACHYCARDIA PACING THERAPY

BACKGROUND OF THE INVENTION

The present invention relates generally to the field of cardiac pacing systems, and more particularly to a cardiac pacing device having pacing control for minimizing a ventricular pause that can follow the delivery of an atrial anti-tachycardia pacing (ATP) therapy.

Modern cardiac pacing devices and systems, such as implantable pacemakers and cardioverter-defibrillators, are designed for efficient dual or multiple chamber pacing, as well as for detection and treatment of dangerous cardiac arrhythmias. A dual chamber pacing device commonly provides an atrial tracking, synchronous pacing mode (such as DDD or DDDR), whereby the ventricle is paced in synchrony with sensed and/or paced atrial activity. This type of pacing scheme approximates the normal healthy coordination between the atrium and the ventricle and, thus, optimizes cardiac output of the heart.

If the atrium is seized with an arrhythmia, however, most modern pacing devices will switch from an atrial tracking, synchronous pacing mode (such as DDD) to a non-tracking, atrial-ventricular (AV) sequential pacing mode (such as DDI), in which the ventricle is paced in response to pulsed atrial activity but not sensed atrial activity. To combat the atrial arrhythmia, the pacing device commonly will select and administer an ATP therapy comprising a plurality of carefully controlled, rapidly administered pulses to the atrium. During delivery of the ATP therapy to the atrium, the pacing device will switch to a special therapy mode (such as AOO with VVI backup) in which the ventricle is paced independent of atrial activity. That is, neither paced nor sensed atrial events trigger pacing in the ventricle. During the special therapy mode, the ventricle is commonly paced at a patient-specific lower rate interval (LRI), or at a sensor rate if the patient's current activity levels justify a higher rate.

Upon delivery of the last atrial pacing pulse of the ATP therapy, the pacing device commonly reverts back to the non-tracking, AV sequential pacing mode (e.g., DDI). This transition back, however, may result in a ventricular pulse-to-ventricular pulse (V-V) interval between the last ventricular pulse delivered prior to the cessation of the ATP therapy and the first ventricular pulse (paced or intrinsic) delivered after completion of the ATP therapy that is significantly longer than the LRI.

This is especially true if the last atrial pulse of the ATP therapy occurs immediately prior to the next scheduled ventricular pulse. This long V-V interval experienced upon transition between the pacing device's therapy mode and non-tracking, AV sequential mode is referred to herein as a ventricular pause.

A ventricular pause that is greater than the LRI presents three potentially negative effects. First, the long ventricular pause may produce undesirable symptoms in some patients. Second, alternating between relatively short and long ventricular intervals could be potentially pro-arrhythmic. Third, the long ventricular pause may result in confusion for the patient's physician because data stored in the device may appear as though the patient was paced at a rate lower than the programmed LRI.

BRIEF SUMMARY OF THE INVENTION

The present invention introduces a pacing control for use in a multiple-chamber cardiac pacing system, which, upon detecting an atrial arrhythmia, automatically switches to a special therapy mode and administers a selected anti-tachycardia pacing (ATP) therapy in the atrium, and which switches to a standard pacing mode following delivery of the ATP therapy. The pacing control adjusts the timing of pacing pulses to be delivered to the atrium and/or the ventricle to minimize any potential ventricular pauses that may result from the switch from the therapy mode to the standard pacing mode.

DETAILED DESCRIPTION

Figure 1:
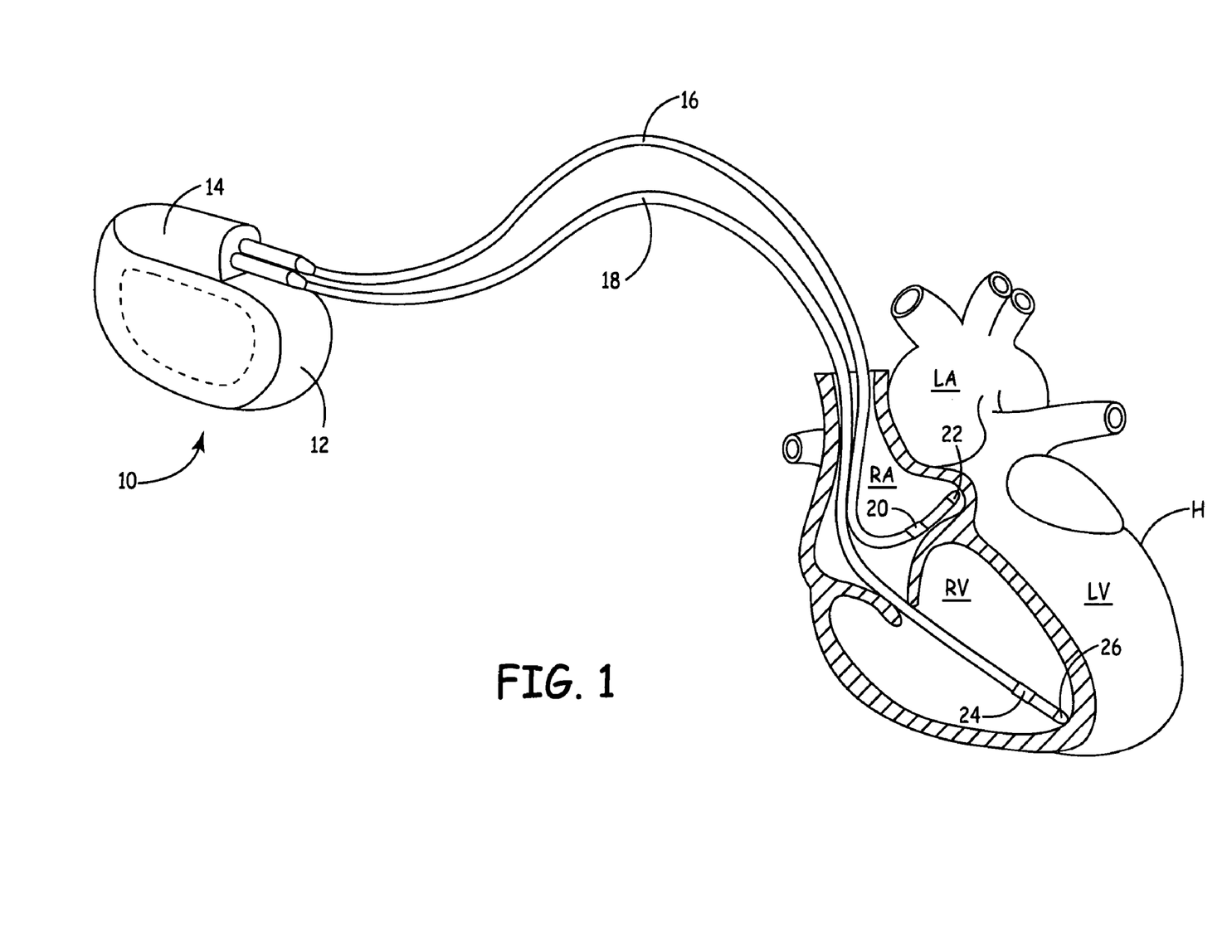
FIG. 1 is a diagram of an implantable medical device and lead set of a type in which the present invention may be practiced.

FIG. 1 is a diagram of implantable medical device (IMD) 10 capable of providing pacing therapy to heart H in accordance with the present invention. IMD 10 is presented herein as one embodiment of a cardiac pacing system that embodies the pacing control of the present invention. However, the pacing control of the present invention may be adapted for use with any multiple chamber pacing or defibrillation system which, upon detecting an atrial arrhythmia, automatically switches from an atrial synchronous pacing mode to a non-tracking pacing mode and administers an anti-tachycardia pacing (ATP) therapy in the atrium, and which reverts to the atrial synchronous pacing mode upon successful termination of the atrial arrhythmia by the ATP therapy.

In the embodiment illustrated in FIG. 1, IMD 10 includes hermetically-sealed housing 12, header 14, right atrial (RA) lead 16, and right ventricular (RV) lead 18. IMD 10 further includes circuitry and a power source, which are located within housing 12, for controlling the operation of IMD 10. The circuitry, which includes the pacing control of the present invention, communicates with leads 16 and 18 through electrical connectors within header 14. Leads 16 and 18 extend from header 14 to right atrium RA and right ventricle RV, respectively, of heart H. Leads 16 and 18 carry one or more sensors/electrodes for sensing electrical signals attendant to the depolarization and repolarization of heart H, and further for providing pacing pulses for causing depolarization of cardiac tissue in the vicinity of the distal ends thereof.

As shown in FIG. 1, atrial electrodes 20 and 22 are disposed at the distal end of RA lead 16 and are located in right atrium RA. Similarly, ventricular electrodes 24 and 26 are disposed at the distal end of RV lead 18 and are located in right ventricle RV.

Figure 2:
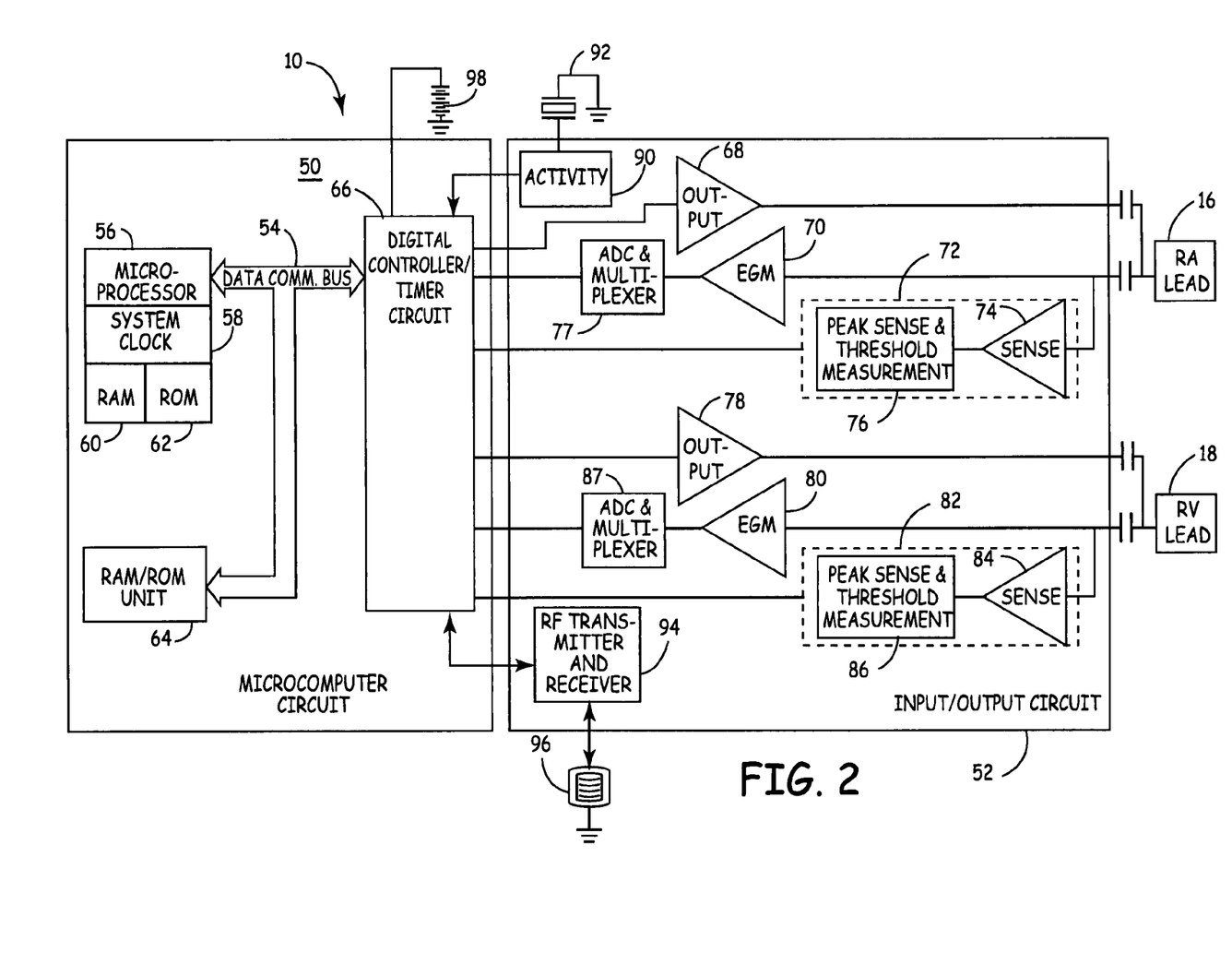
FIG. 2 is a functional block diagram of the circuitry of the implantable medical device of FIG. 1.

FIG. 2 is a functional block diagram of the circuitry located within IMD 10. This block diagram is intended to be merely exemplary and corresponds only to a general functional organization of most presently available IMDs. The circuitry generally includes microcomputer circuit 50, input/output circuit 52, and data communications bus 54.

Microcomputer circuit 50 includes microprocessor 56, system clock 58, on-board RAM memory 60, on-board ROM memory 62, off-board RAM/ROM memory 64, and digital controller/timer circuit 66 connected to microprocessor 56 and off-board RAM/ROM memory 64 via data communications bus 54. Microcomputer circuit 50 communicates with input/output circuit 52 to monitor electrical activity in heart H as well as to deliver appropriately-timed pulses to the various electrodes. Digital controller/timer circuit 66 includes digital timers and counters used to determine time between successive depolarizations in the atria and ventricles, as well as to provide various refractory, blanking, and other timing windows used to determine delivery of paced pulses to the atria and ventricles. Digital controller/timer circuit 66 receives sensed activity signals and causes pacing pulses to be delivered via connections to leads 16 and 18.

RA lead 16 is connected to digital controller/timer circuit 66 via output pulse generator 68, electrogram (EGM) amplifier 70, and sensing circuitry 72. Sensing circuitry 72 includes sense amplifier 74 and peak sense and threshold measurement circuitry 76. Sense amplifier 74 amplifies electrical cardiac signals sensed by RA lead 16 and provides an amplified signal to peak sense and threshold measurement circuitry 76, which in turn provides an indication of sensed cardiac events and measured sense amplifier threshold voltages to digital controller/timer circuit 66. Electrical signals sensed by RA lead 16 provide microcomputer 50 with information regarding depolarizations in right atrium RA. Signals received by RA lead 16 are also provided to EGM amplifier 70 and are converted into digital values by analog-to-digital converter (ADC) and multiplexer 77. The output of ADC and multiplexer 77 provides a digitized version of the EGM signal, which IMD 10 may transmit to an external programmer (not shown) when interrogated by the external programmer to transmit a representation of a cardiac EGM. Under the control of microcomputer circuit 50 and digital controller/timer circuit 66, output pulse generator 68 provides pacing pulses to RA lead 16.

In a similar fashion, RV lead 18 is also connected to digital controller/timer circuit 66 via output pulse generator 78, EGM amplifier 80, and sensing circuitry 82. Sensing circuitry 82 includes sense amplifier 84 and peak sense and threshold measurement circuitry 86.

Sense amplifier 84 amplifies electrical cardiac signals sensed by RV lead 18 and provides an amplified signal to peak sense and threshold measurement circuitry 86, which in turn provides an indication of sensed cardiac events and measured sense amplifier threshold voltages to digital controller/timer circuit 66. Electrical signals sensed by RV lead 18 provide microcomputer 50 with information regarding depolarizations in right ventricle RV. Signals received by RV lead 18 are also provided to EGM amplifier 80 and are converted to a digital value by ADC and multiplexer 87. The output of the ADC and multiplexer 87 provides a digitized version of the EGM signal, which IMD 10 may transmit to the external programmer when interrogated by the external programmer to transmit a representation of a cardiac EGM. Under the control of microcomputer circuit 50 and digital controller/timer circuit 66, output pulse generator 78 provides pacing pulses to RV lead 18.

In the embodiment shown in FIG. 2, IMD 10 also includes activity sensor 90 and accelerometer 92 or activity crystal, which provide input to digital controller/timer circuit 66 regarding a patient's metabolic requirements. Digital controller/timer circuit 66 takes into account input from activity sensor 90 and accelerometer 92 in deciding an appropriate rate at which to provide pulses to RA lead 16 and RV lead 18. However, the patient preferably is not paced at a rate lower than a programmed, patient-specific, lowest rate interval (LRI).

IMD 10 also includes RF transmitter and receiver 94 and antenna 96, which allows IMD 10 to be programmed by means of an external programming unit (not shown). Power is supplied to all systems of IMD 10 by power supply 98.

IMD 10 may implement any of a number of different pacing modes depending on the situation. Digital controller/timer circuit 66 of FIG. 2 includes programmable digital counters that control the basic timing intervals associated with each of the various pacing modes. Each mode can be described by a three-letter (or sometimes four) code as described in the following table:

|  | Digit | | |
| --- | --- | --- | --- |
|  | 1 | 2 | 3 |
| Function | Chamber Paced | Chamber Sensed | Pacing Response |
| Options | A—Atrium | A—Atrium | T—Triggered |
|  | V—Ventricle | V—Ventricle | I—Inhibited |
|  | D—Both | D—Both | D—Both |

For example, when operating in a DDD mode (known as a tracking mode), IMD 10 may pace either the atrium or the ventricle and senses in either the atrium or the ventricle. In response to sensed depolarizations, pulses may be triggered or inhibited. Thus, IMD 10 operating in the DDD mode may deliver pacing pulses to right ventricle RV in response to electrical activity sensed (intrinsic or paced) in right atrium RA. During normal operation of IMD 10, this tracking mode is a common pacing strategy to maintain a one-to-one coordination between atrial and ventricular contractions.

Figure 3:
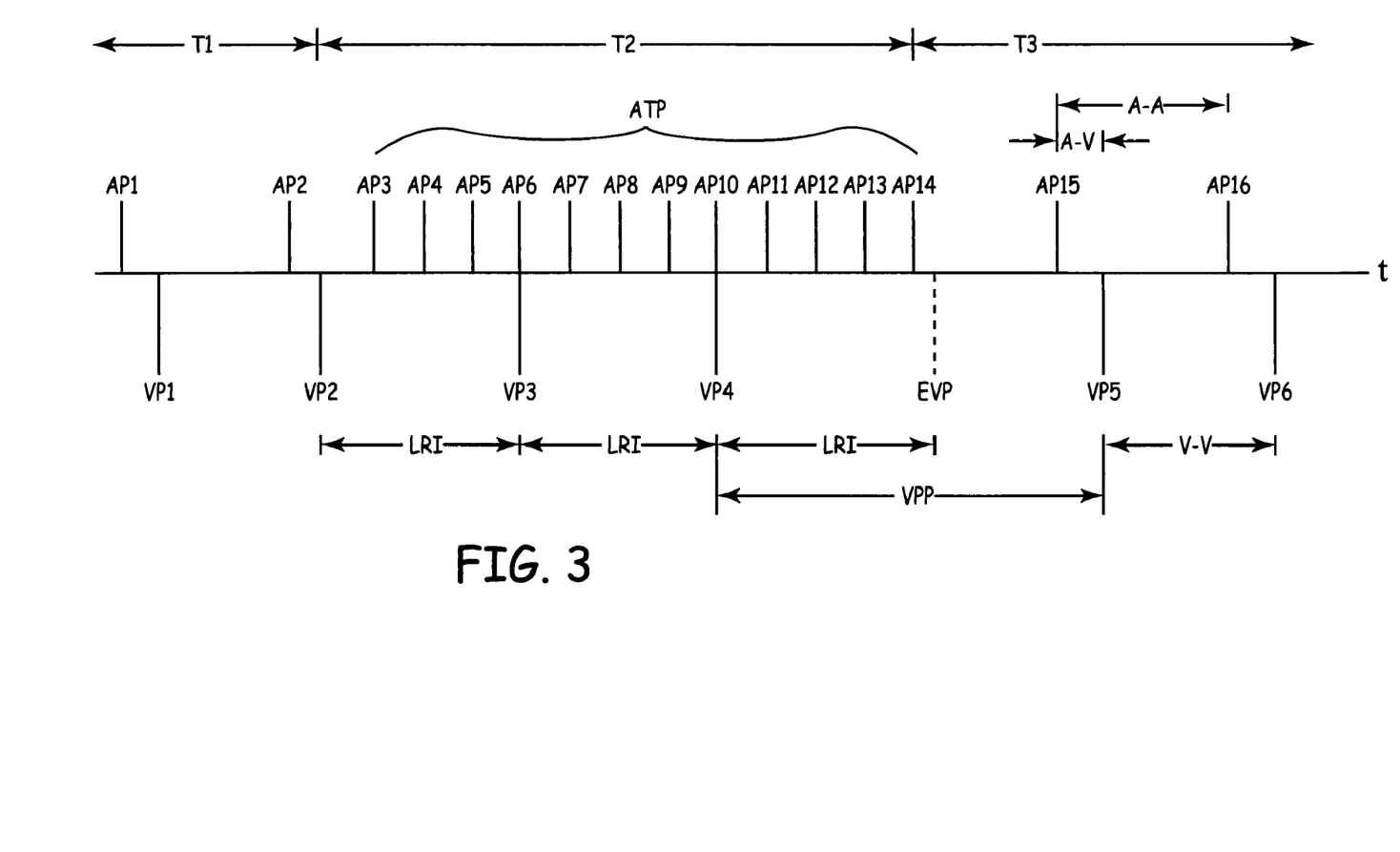
FIG. 3 is an example of a timing diagram for illustrating a ventricular pause that can follow the delivery of an atrial anti-tachycardia pacing therapy.

FIG. 3 is an example of a timing diagram illustrating atrial pacing pulses AP1-AP16 (collectively AP) and ventricular pacing pulses VP1-VP6 (collectively VP) for delivery by IMD 10 to right atrium RA and right ventricle RV, respectively, as a function of time over first, second, and third periods T1-T3.

During first and third periods T1 and T3, IMD 10 operates in a non-tracking, AV sequential pacing mode such as DDI. This mode is commonly used when IMD 10 is following detection of an atrial arrhythmia. During the non-tracking, AV sequential mode, ventricular pacing pulses VP are delivered by IMD 10 only in response to paced atrial pulses, and not to sensed atrial pulses.

In the example shown in FIG. 3, IMD 10 detects an arrhythmia (not shown) in right atrium RA prior to first time period T1. Upon detection of this atrial arrhythmia, IMD 10 automatically switches to a non-tracking, AV sequential mode (period 1). To combat the atrial arrhythmia, IMD 10 automatically selects an appropriate ATP therapy and begins delivery of the selected ATP therapy to right atrium RA during second time period T2. At the onset of period T2, IMD 10 switches modes to a special therapy mode in which ventricular pacing pulses VP are provided independent of atrial pulses AP (i.e., a non-tracking mode with no AV synchronization). ATP therapies may vary depending upon the device's programmed setting and the detection rate of the arrhythmia, but generally include a carefully controlled, rapidly paced sequence of pacing pulses. In this example, the selected ATP therapy consists of rapidly-paced pulses AP3-AP14.

Independent of this activity in right atrium RA, IMD 10 paces right ventricle RV at a constant, patient-specific lower rate interval (LRI) representing the lowest rate at which the patient should be paced. If justified by the patient's current activity levels, however, right ventricle RV may be paced at a higher activity-based rate.

As shown in FIG. 3, expected ventricular pacing pulse EVP is scheduled for delivery shortly after last atrial pulse AP14 of the ATP therapy. However, following delivery of the ATP therapy, IMD 10 switches back to its non-tracking, AV sequential mode in which ventricular pacing pulses VP lag behind atrial pacing pulses AP, delivered by IMD device 10, by the A-V interval. During the mode transition between the therapy mode and the non-tracking, AV sequential mode, IMD 10 enforces "A-A timing", in which atrial pulses are provided at the programmed rate at the expense of providing ventricular pulses at the programmed rate. Therefore, atrial pulse AP15 is delivered after the last atrial pulse in the ATP therapy (AP14) at an interval defined by the atrial programmed rate. This mode transition, with A-A timing enforced, causes expected ventricular pulse EVP to not be delivered to the ventricle and thus results in a V-V interval between ventricular pacing pulses VP4 and VP5 that is significantly longer than the LRI. It is this long interval that is referred to herein as ventricular pause VPP.

Conventionally, atrial ATP therapies were delivered without any consideration of potential ventricular pauses VPP. As described above, however, this long V-V interval, or ventricular pause VPP, may have some undesirable effects.

Figure 4:
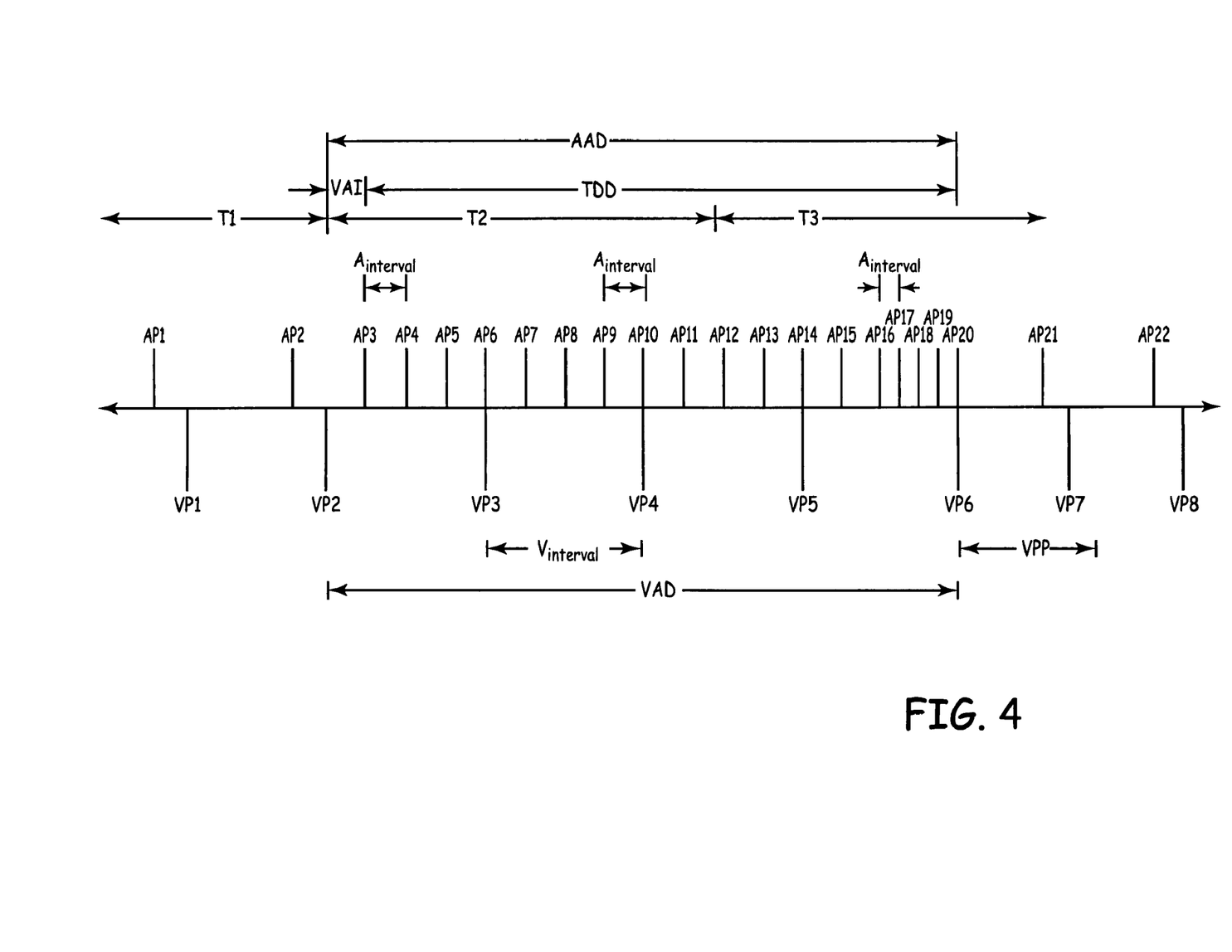
FIGS. 4, 5A and 5B are examples of timing diagrams for illustrating a pacing control in accordance with the present invention for use in the implantable medical device.

FIG. 4 is an example of a timing diagram for illustrating a pacing control of IMD 10 for minimizing potential ventricular pauses in accordance with the present invention. The pacing control of the present invention is based upon the premise that IMD 10 can calculate the timing of a selected atrial ATP therapy and can adjust the timing of pacing pulses to be delivered to right atrium RA and/or right ventricle RV to minimize the ventricular pause VPP.

As shown in FIG. 4, the therapy delivery duration (TDD) of a selected atrial ATP therapy is a function of the number (n) of ATP pulses comprising the ATP therapy and the mean A-A interval ($MA_{interval}$) between successive ATP pulses as follows:

$$TDD = n \cdot MA_{interval}$$

By adding this duration to an initial V-A interval (VAI), an atrial activity duration (AAD) can be determined as follows:

$$AAD = TDD + VAI = n \cdot MA_{interval} + VAI$$

In this formula, the V-A interval (VAI) is the interval occurring between the ventricular pulse delivered just prior to ATP therapy delivery (VP2) and the first ATP pulse of the ATP therapy (AP3). A corresponding ventricular activity duration (VAD) during this ATP therapy delivery can be determined as a function of the number of ventricular beats (Z) that would normally occur in the selected ATP therapy and the V-V interval ($V_{interval}$) between successive ventricular pulses as follows:

$$VAD = Z \cdot V_{interval}$$

The pacing control of the present invention then attempts to minimize potential ventricular pauses VPP by selecting a value for one of the five variables, of which the atrial activity duration (AAD) and the ventricular activity duration (VAD) are a function, that best equalizes these two durations as follows:

$$n \cdot MA_{interval} + VAI = Z \cdot V_{interval}$$

In other words, the goal in this embodiment is to cause the last ventricular pulse provided during delivery of the ATP therapy to fall simultaneous with, or shortly before, the last ATP pulse of the selected ATP therapy. In alternate embodiments, the final ventricular pulse may occur at a prescribed offset with respect to the final ATP therapy pulse. However, this offset should be minimized to keep the potential ventricular pause as small as possible.

Following are several approaches by which a selected atrial ATP therapy and/or ventricular pacing schedule may be adjusted in accordance with the present invention to minimize potential ventricular pauses. In each of the hypothetical examples presented below, the default values defining the ATP therapy are as follows: the mean A-A interval ($MA_{interval}$) is 150 milliseconds, the number of atrial ATP pulses (n) is 25, the initial V-A interval (VAI) is 110 milliseconds, and the V-V interval ($V_{interval}$) is 1000 milliseconds.

Approach 1: V-V Interval

A first approach provides that an alternate V-V interval ($V_{interval}$) be determined for pacing ventricular pulses VP during delivery of the atrial ATP therapy. In many pacing systems, the V-V interval ($V_{interval}$) is a pre-programmed value determined by the physician for a particular patient. To prevent the physician's settings from being overridden by the pacing control of the pacing system, the pacing system may instead request that the physician program a range of acceptable V-V intervals ($V_{interval}$) for the patient. In this scenario, the first step is then to determine an intermediate number of ventricular pacing pulses (Z') that will result in a V-V interval ($V_{interval}$) in the acceptable range of V-V intervals ($V_{interval}$). In the hypothetical example presented above, this calculation would be as follows:

$$Z' = (n \cdot MA_{interval} + VAI)/V_{interval}$$

$$Z' = [(25 \cdot 150 \text{ ms}) + 110 \text{ ms}]/1000 \text{ ms} = 3.86 \text{ pulses}$$

The fact that this result is a non-integer value indicates that a ventricular pause would exist if none of the above variables were adjusted. Rather, in accordance with the present invention, the number of ventricular pacing pulses (Z) is determined by rounding the intermediate number of ventricular pacing pulses (Z') to an integer value.

A modified V-V interval ($V_{interval}'$) is then calculated as:

$$V_{interval}' = (n \cdot MA_{interval} + VAI)/Z'$$

$$V_{interval}' = [(25 \cdot 150 \text{ ms}) + 110 \text{ ms}]/4 = 965 \text{ ms}$$

Thus, by adjusting the V-V interval ($V_{interval}$) to 965 milliseconds (rather than the default 1000 milliseconds), the last ventricular pulse during atrial ATP therapy and the last atrial pulse of the ATP therapy will be delivered at substantially the same time. Further, by rounding the unadjusted number of ventricular pulses up to the next highest integer, the modified V-V interval ($V_{interval}'$) is assured to be shorter (i.e., faster) than the LRI.

The method in which IMD 10 rounds the intermediate number of ventricular pacing pulses (Z') to an integer value affects the selected V-V interval ($V_{interval}$). In a first method, IMD 10 rounds the intermediate number of ventricular pacing pulses (Z') to the nearest integer, causing the V-V interval ($V_{interval}$) to be maintained close to its programmed setting. In a second method, the intermediate number of ventricular pacing pulses (Z') is rounded to the next highest integer (e.g., 3.25 would be rounded to 4), ensuring the V-V interval ($V_{interval}$) is maintained at a rate faster than the lower rate interval (LRI). Although the second method ensures the V-V interval ($V_{interval}$) falls within accepted parameters, it causes greater deviation from the programmed rate.

In one embodiment, IMD 10 initially employs the first method and rounds the intermediate number of ventricular pacing pulses (Z') to the nearest integer. If the resulting V-V interval ($V_{interval}$) (or other modified parameter) falls within an acceptable range, then IMD 10 proceeds to deliver the ventricular pacing pulses at the modified V-V interval ($V_{interval}$). If however, the resulting V-V interval ($V_{interval}$) does not fall within an acceptable range (e.g., modified V-V interval ($V_{interval}$) is below the LRI by a sufficient amount), then IMD 10 rounds the intermediate number of ventricular pacing pulses (Z') the next higher integer to ensure a V-V interval within the accepted range.

Approach 2: Number of ATP Therapy Pulses

A second approach adjusts the number of ATP therapy pulses (n) to minimize potential ventricular pauses VPP. Specifically, a small number of the intended ATP therapy pulses are either withheld or added in an attempt to equalize the atrial activity duration (AAD) with the ventricular activity duration (VAD). Once again, the first step is to determine an intermediate number of ventricular pacing pulses (Z') that will result in a V-V interval ($V_{interval}$) in the acceptable range of V-V intervals ($V_{interval}$). Turning to the hypothetical, as shown in the first approach presented above, the intermediate number of ventricular pacing pulses (Z') is 3.86, which is then rounded to the nearest integer value or the next higher integer value (depending on the method selected by IMD 10) to determine the number of ventricular pacing pulses (Z) to be delivered as four.

A modified number of ATP therapy pulses (n') is then calculated as:

$$n'=[(Z'*V_{interval})-VAI]/MA_{interval}$$

$$n'=[(4*1000\text{ ms})-110\text{ ms}]/150\text{ ms}=25.93$$

As discussed with respect to Approach 1, rounding to the nearest integer results in the modified number of ATP therapy pulses (n') being maintained closer to the programmed value. However, this method may result in fewer ATP therapy pulses (n') being delivered. By rounding to the next highest integer, the modified number of ATP therapy pulses (n') will always be equal to or greater than the original number of ATP therapy pulses (n). Rounding the number of ventricular pacing pulses to the nearest integer value (in this case, four) results in twenty-six ATP therapy pulses (rather than the default twenty-five pulses) being delivered to the atrium. Thus, by adding just one additional ATP therapy pulse, the potential ventricular pause VPP is substantially minimized. Because of this final rounding of the number of ATP therapy pulses, however, the ventricular pause will not be completely eliminated. The number of ATP therapy pulses (n') may differ slightly from the programmed number of ATP therapy pulses when using this approach.

In one embodiment, the number of ATP therapy pulses (n) to be included in particular ATP therapies may be programmed as discrete range of values rather than exact numbers, allowing flexibility in determining the number of ATP therapy pulses to be included in a particular ATP therapy.

Approach 3: Mean A-A Interval

A third approach provides that the mean A-A interval ($MA_{interval}$) be adjusted so that the atrial activity duration (AAD) substantially equals the ventricular activity duration (VAD). Once again, an intermediate number of ventricular pulses (Z') is determined to be 3.86 pulses. In this third approach, however, this intermediate value is preferably rounded to the nearest integer value (rather than the next highest integer value).

Despite this distinction, the number of ventricular pacing pulses (Z) in this example is still four.

A modified mean A-A interval ($MA_{interval}'$) is then calculated as:

$$MA_{interval}'=[(Z'*V_{interval})-VAI]/n$$

$$MA_{interval}'=[(4*1000\text{ ms})-110\text{ ms}]/25=155.6\text{ ms}$$

Depending upon the resolution of the pacing system, this value may need to be rounded to the nearest acceptable value. For example, if the resolution is five milliseconds, the modified mean A-A interval ($MA_{interval}'$) would be rounded to 155 milliseconds, but if the resolution were ten milliseconds, the modified mean A-A interval ($MA_{interval}'$) would be rounded to 160 milliseconds.

Thus, potential ventricular pauses VPP may be minimized by slightly increasing or decreasing the mean A-A interval ($MA_{interval}$) of the ATP therapy pulses. In one embodiment, mean A-A interval ($MA_{interval}$) between the delivered ATP pulses is allowed to vary from programmed values for the A-A intervals between successive ATP pulses. In alternate embodiments, the mean A-A interval ($MA_{interval}$) is programmed as a discrete range rather than an exact number.

Approach 4: Initial V-A Interval

This fourth approach delays the initiation of the ATP therapy by adjusting the initial V-A interval (VAI) to improve the relative timing of the end of the ATP therapy. Again, an intermediate number of ventricular pulses (Z') is determined to be 3.86 pulses, which value is then rounded to the nearest integer to provide for four ventricular pacing pulses.

A modified initial V-A interval (VAI') is then calculated as:

$$VAI'=(Z'*V_{interval})-(n*MA_{interval})$$

$$VAI'=(4*1000\text{ ms})-(25*150\text{ ms})=250\text{ ms}$$

Depending upon the resolution of the pacing system, this value may need to be rounded to the nearest acceptable value. In implementing this approach, a timer set for this value begins running after the last ventricular pulse delivered prior to the delivery of the ATP therapy. Once the timer expires, the pacing system would begin delivering the atrial ATP therapy. By slightly shifting the delivery of the ATP therapy, the duration of any potential ventricular pause can be minimized.

Approach 5: Shift Pause to Atrium

Figure 5A:
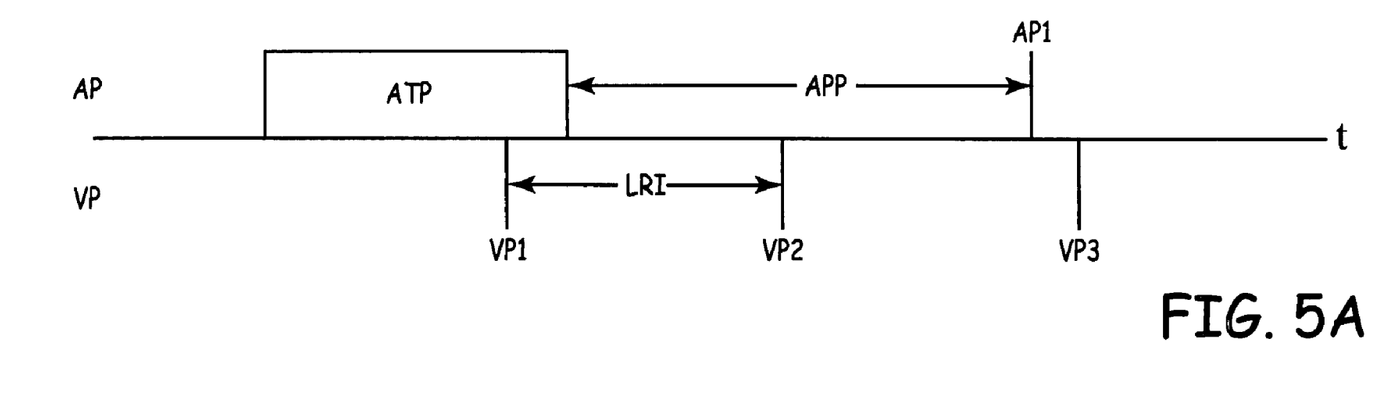
Figure 5B:
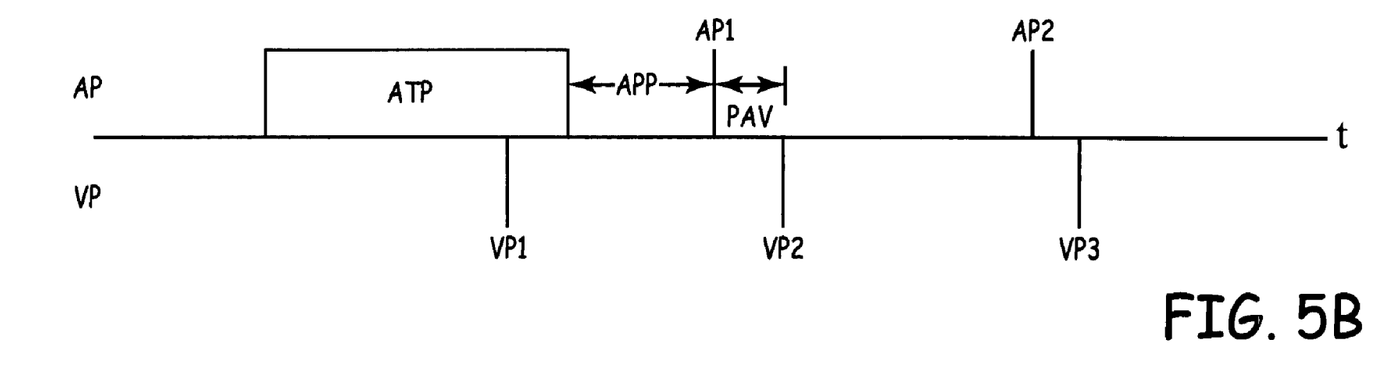

FIGS. 5A and 5B are timing diagrams illustrating a fifth approach to minimizing potential ventricular pauses following the transition from a non-tracking mode during delivery of an atrial ATP therapy to an atrial synchronous mode. Rather than adjusting the timing of pacing pulses to be delivered to right atrium RA and/or right ventricle RV during the time the ATP therapy is being delivered, this fifth approach modifies the timing of the pacing pulses immediately following the ATP therapy delivery.

As described above, pacing activity in the ventricle, when operating in the atrial synchronous mode, generally tracks pacing activity in the atrium. For this reason, following successful termination of an atrial arrhythmia by an ATP therapy and return to the atrial synchronous mode, conventional pacing systems enforcing A-A timing first schedule an atrial pacing pulse AP, which may then be tracked by a ventricular pacing pulse VP. Because A-A timing does not take into account the ventricular programmed rate, a long ventricular pause can result following a switch of modes.

In this fifth approach, following delivery of the ATP therapy, the pacing system schedules a ventricular pacing pulse VP to occur prior to any atrial pacing pulses AP. As shown in FIG. 5A, following the delivery of a successful ATP therapy (and consequent return to the tracking mode), ventricular pacing pulse VP2 is scheduled at the LRI rate from ventricular pulse VP1, which is the last ventricular pulse delivered during delivery of the ATP therapy. First post-ATP atrial pulse AP1 is then scheduled from the first post-ATP ventricular pulse VP2, followed by conventional atrial synchronous mode pacing (employing A-A timing) in both the atrium and the ventricle. This approach may increase the interval between the last atrial pulse delivered as part of the ATP therapy and the next atrial pulse (e.g., AP1). It is believed by the present inventors, however, that a potential pause in the atrium is less worrisome than a long pause in the ventricle and that this may be a viable option for certain patients.

FIG. 5B illustrates an alternative to the method illustrated in FIG. 5A, in which the long atrial pause described with respect to FIG. 5A is minimized by employing V-V timing. In V-V timing, ventricular pulses are delivered at the programmed rate (i.e., LRI as shown in FIG. 5B) at the expense of the atrial programmed rate. As shown in FIG. 5B, following the delivery of a successful ATP therapy (and consequent return to the tracking mode), ventricular pacing pulse VP2 is scheduled at the LRI from ventricular pulse VP1, which is the last ventricular pulse delivered during delivery of the ATP therapy. Because V-V timing is being enforced, a first post-ATP atrial pulse is scheduled to occur at the pulsed atrial-ventricular interval (PAV) prior to delivery of the ventricular pulse VP2. The benefit of this method is the return to synchronous pacing directly following delivery of the ATP therapy, as well as a reduction in the atrial pause described with respect to FIG. 5A when A-A timing is enforced. However, because V-V timing is being enforced, the first post-ATP atrial pulse (AP1) may be delivered close in time with a previous atrial pulse delivered as part of the ATP therapy.

Sensed Ventricular Pulses

For sake of simplicity, it is assumed in describing the above approaches that ventricular pacing occurs throughout the duration of the ATP therapy, that is, that no intrinsic pulses are detected in the ventricle. It is possible, however, that intrinsic pulses may be sensed in the ventricle, causing a planned paced pulse to be inhibited. Where ventricular sensing occurs, the above described calculations could be performed dynamically, or 'on the fly', to continually adjust the timing of the delivered pacing pulses to minimize potential ventricular pauses. Of course, if intrinsic ventricular pulses are consistently occurring, long ventricular pauses are unlikely to result because the patient would appear to have adequate A-V conduction.

Although the present invention has been described with reference to preferred embodiments, workers skilled in the art will recognize that changes may be made in form and detail without departing from the spirit and scope of the invention. For example, although the present invention was described above with respect to an implantable pacemaker device, the invention is equally adaptable for use in both implantable and external pacing systems. Further, the illustrated embodiments show pacing in only right atrium RA and right ventricle RV, but the present invention applies equally to pacing in all four chambers of the heart.

The invention claimed is:

1. A cardiac pacing device comprising:
an atrial lead and an atrial electrode mounted with respect to the atrial lead;
a ventricular lead and a ventricular electrode mounted with respect to the ventricular lead;
a sensor, operatively coupled to at least one of the atrial electrode and the ventricular electrode, sensitive to an atrial arrhythmia;
pulse generation circuitry connected to the atrial and ventricular electrodes delivering an anti-tachycardia pacing (ATP) therapy in response to the atrial arrhythmia comprising a plurality of atrial pulses defined by at least one atrial pacing parameter and a plurality of ventricular pulses defined by at least one ventricular pacing parameter and a synchronous therapy following a termination of the anti-tachycardia pacing (ATP) therapy, the synchronous therapy comprising a plurality of atrial pulses and a corresponding plurality of ventricular pulses, each of the ventricular pulses having a predetermined timing relationship following a corresponding one of the plurality of atrial pulses; and
control circuitry operatively coupled to the pulse generation circuitry adjusting a priori at least one of the at least one atrial pacing parameter and the at least one ventricular pacing parameter, based on the at least one atrial pacing parameter and the at least one ventricular pacing parameter, to make a last individual one of the plurality of ventricular pulses approximately coincident with a last individual one of the plurality of atrial pulses at the termination of the anti-tachycardia pacing (ATP) therapy.

2. The cardiac pacing device of claim 1, wherein the control circuitry adjusts at least one of the at least one atrial pacing parameter and of the at least one ventricular pacing parameter in response to a detected intrinsic depolarization in the ventricle.

3. The cardiac pacing device of claim 1, wherein the control circuitry causes the pulse generation circuitry, in response to a detected atrial arrhythmia, to switch from delivering the synchronous therapy to delivering the anti-tachycardia pacing therapy, and wherein the control circuitry further causes the pulse generation circuitry to deliver the synchronous therapy after the last individual one of the plurality of atrial pulses.

4. The cardiac pacing device of claim 1, wherein the at least one ventricular pacing parameter includes a number of ventricular pulses comprising the plurality of ventricular pacing pulses.

5. The cardiac pacing device of claim 1, wherein the at least one atrial pacing parameter includes a number of atrial pulses comprising the plurality of ventricular pacing pulses.

6. The cardiac pacing device of claim 1, wherein the at least one ventricular pacing parameter includes a time interval between successive individual ones of the plurality of ventricular pulses.

7. The cardiac pacing device of claim 1, wherein the at least one atrial pacing parameter includes a mean time interval between successive individual ones of the plurality of atrial pulses.

8. The cardiac pacing device of claim 1, wherein the at least one ventricular pacing parameter includes a time interval between a ventricular pulse delivered or sensed immediately preceding delivery of the ATP therapy and a start of the ATP therapy.

9. The cardiac pacing device of claim 1, wherein the at least one atrial pacing parameter includes a time interval between a last individual one of the plurality of atrial pulses and a first atrial pacing pulse following the ATP therapy.

10. A method for use with a cardiac pacing device in pacing an atrium and a ventricle of a patient, the method comprising the steps of:
    detecting an atrial arrhythmia; then
    delivering an anti-tachycardia pacing (ATP) therapy in response to the atrial arrhythmia comprising a plurality of atrial pulses defined by at least one atrial pacing parameter and a plurality of ventricular pulses defined by at least one ventricular pacing parameter; then
    delivering a synchronous therapy following a termination of the anti-tachycardia pacing (ATP) therapy, the synchronous therapy comprising a plurality of atrial pulses and a corresponding plurality of ventricular pulses, each of the ventricular pulses having a predetermined timing relationship following a corresponding one of the plurality of atrial pulses; and
    wherein the delivering an anti-tachycardia pacing (ATP) therapy step is modified a priori based on the at least one atrial pacing parameter and the at least one ventricular pacing parameter by adjusting at least one of an individual one of the at least one atrial pacing parameter and of the at least one ventricular pacing parameter to make a last individual one of the plurality of ventricular pulses approximately coincident with a last individual one of the plurality of atrial pulses at the termination of the anti-tachycardia pacing (ATP) therapy.

11. The method of claim 10 further comprising the step of:
    sensing an intrinsic depolarization in the ventricles; and
    wherein the delivering an anti-tachycardia pacing (ATP) therapy step adjusts at least one of an individual one of the at least one atrial pacing parameter and of the at least one ventricular pacing parameter in response to a detected intrinsic depolarization in the ventricle.

12. The method of claim 10 wherein the at least one of an individual one of the at least one atrial pacing parameter and of the at least one ventricular pacing parameter is at least one of a number of ventricular pulses comprising the plurality of ventricular pulses; a number of the plurality of atrial pulses; a time interval between successive individual ones of the plurality of ventricular pulses; a mean time interval between successive individual ones of the plurality of atrial pulses; a time interval between a ventricular pulse immediately preceding delivery of the ATP therapy and a start of the ATP therapy; and a time interval between a last individual one of the plurality of atrial pulses of the ATP therapy and a first atrial pacing pulse immediately following the ATP therapy.

13. A cardiac pacing device for use with a patient, the cardiac pacing device comprising:
    means for detecting an atrial arrhythmia;
    means for delivering an anti-tachycardia pacing (ATP) therapy in response to the atrial arrhythmia comprising a plurality of atrial pacing pulses defined by at least one atrial pacing parameter and a plurality of ventricular pulses defined by at least one ventricular pacing parameter; then
    means for delivering a synchronous therapy following a termination of the anti-tachycardia pacing (ATP) therapy, the atrial sensing therapy comprising a plurality of atrial pacing pulses and a corresponding plurality of ventricular pulses, each of the ventricular pacing pulses having a predetermined timing relationship following a corresponding one of the plurality of atrial pacing pulses;
    wherein the means for delivering an anti-tachycardia pacing (ATP) therapy modify a priori at least one of an individual one of the at least one atrial pacing parameter and of the at least one ventricular pacing parameter, based on the at least one atrial pacing parameter and the at least one ventricular pacing parameter, to make a last individual one of the plurality of ventricular pacing pulses approximately coincident with a last individual one of the plurality of atrial pacing pulses at the termination of the anti-tachycardia pacing (ATP) therapy.

14. The cardiac pacing device of claim 13 and further comprising:
    means for sensing an intrinsic depolarization in the ventricle; and
    wherein the means for delivering an anti-tachycardia pacing (ATP) therapy modifies at least one of an individual one of the at least one atrial pacing parameter and of the at least one ventricular pacing parameter in response to a detected intrinsic depolarization in the ventricle.

15. The cardiac pacing device of claim 13 wherein the at least one of an individual one of the at least one atrial pacing parameter and of the at least one ventricular pacing parameter is at least one of a number of ventricular pulses comprising the plurality of ventricular pacing pulses; a number of the plurality of atrial pulses; a time interval between successive individual ones of the set of ventricular pulses; a mean time interval between successive individual ones of the plurality of atrial pulses therapy; a time interval between a ventricular pulse immediately preceding delivery of the ATP therapy and a start of the ATP therapy; and a time interval between the last individual one of the plurality of atrial pulses of the ATP therapy and a first atrial pacing pulse immediately following the ATP therapy.

* * * * *